US00RE39788E

(19) United States
(12) Reissued Patent
Anderson et al.

(10) Patent Number: US RE39,788 E
(45) Date of Reissued Patent: Aug. 21, 2007

(54) GENE THERAPY

(75) Inventors: W. French Anderson, Bethesda, MD (US); R. Michael Blaese, Rockville, MD (US); Steven A. Rosenberg, Potomac, MD (US)

(73) Assignee: The United States of America as represented by the Department of Health and Human Services, Washington, DC (US)

(21) Appl. No.: 10/701,022

(22) Filed: Nov. 4, 2003

Related U.S. Patent Documents

Reissue of:
(64) Patent No.: 5,399,346
Issued: Mar. 21, 1995
Appl. No.: 08/220,175
Filed: Mar. 30, 1994

U.S. Applications:
(63) Continuation of application No. 07/904,662, filed on Sep. 8, 1992, now abandoned, which is a continuation-in-part of application No. 07/868,794, filed on Apr. 15, 1992, now abandoned, which is a continuation-in-part of application No. 07/807,446, filed on Dec. 13, 1991, now abandoned, which is a continuation-in-part of application No. 07/365,567, filed on Jun. 14, 1989, now abandoned.

(51) Int. Cl.
*A61K 48/00* (2006.01)
*C12N 5/22* (2006.01)
*C12N 15/63* (2006.01)
*C12N 15/09* (2006.01)

(52) U.S. Cl. ..... 424/93.21; 424/93.71; 424/93.2; 435/69.5; 435/69.51; 435/69.52; 435/325; 435/372.3; 435/320.1; 435/455

(58) Field of Classification Search ..... 424/93.2, 424/93.21; 514/44; 435/325, 320.1, 455
See application file for complete search history.

(56) References Cited

FOREIGN PATENT DOCUMENTS

WO WO 87/00201 1/1987

OTHER PUBLICATIONS

Siegel, Los Angeles Times, Dec. 14, 1987, "Desire to be First Colors Gene Studies" pp. 1,22–25.*
Buden, The Scientist, Jan. 23, 1989, "Controversy Surrounds Gene Therapy Effort", pp. 1–3.*
Siegel, Los Angeles Times, Dec. 13, 1987, "Egos, Prizes on the Line for Scientists", pp. 1, 37–40.*
Anderson, John W., The Nation, Apr. 10, 1989, "Scrambling for BioTech Bucks", pp. 476–478.*
Selden, N. Eng. J. Med., vol. 318, No. 20, pp. 1337–1338.*
Thompson, Time, Jun. 7, 1993 "The First Kids With New Gene" pp. 50–53.*
Anderson, *The Nation,* pp. 476–478 (Apr. 10, 1989).
Buden, *The Scientist,* pp. 1–3 (Jan. 23, 1989).
Culver et al., *J. Cell Biochem.,* Supp 12(B), 171 (1988).
Kohn et al., *J. Cell Biochem.,* Supp. 12(B), 178 (1988).
Selden et al., *N. Eng. J. Med.,* 318(20): 1337–1338.
Siegel, *Los Angeles Times,* pp. 1, 22–25 (Dec. 14, 1987).
Siegel, *Los Angeles Times,* pp. 1, 37–40 (Dec. 13, 1987).
Thompson, *Time,* pp. 50–53 (Jun. 7, 1993).
Anderson et al., *Human Gene Therapy, 1,* 331–362 (1990).
Anderson, "Gene Therapy: The Best of Times the Worst of Times," downloaded from the internet on Apr. 5, 2001 at 17:49 hours.
Cline, *Pharmac. Ther., 29,* 69–92 (1985).
Eppstein List of Prior Art References, submitted in Interference No. 104,711.
Gura, *Science, 291,* 1692–1697 (2001).
Marshall, *Science, 288,* 951–957 (2000).
Morgan et al., *Science, 237,* 1476–1479 (1987).
Morgan List of Prior Art Reference, submitted in Interference No. 104,712.
Palmer et al., *Proc. Natl. Acad. Sci. USA, 84,* 1055–1059 (1987).
Rosenberg, "Gene Therapy of Patients with Advanced Cancer Using Tumor Infiltrating Lymphocytes Transduced with the Gene Coding for Tumor Necrosis Factor," Jul. 6, 1990.
Rosenberg et al., *New Engl. J. Med., 323,* 570–578 (1990).
Weiss, "New Rule for Gene Therapy Tests Proposed," downloaded from the internet on Jan. 18, 2001 at 06:52 hours.

* cited by examiner

*Primary Examiner*—Anne M. Wehbe
(74) *Attorney, Agent, or Firm*—Leydig, Voit & Mayer

(57) ABSTRACT

Primary human cells which are genetically engineered with DNA (RNA) encoding a marker or therapeutic which is expressed to be expressed in vivo. Such engineered cells may be used in gene therapy.

6 Claims, 7 Drawing Sheets

GENE THERAPY

Matter enclosed in heavy brackets [ ] appears in the original patent but forms no part of this reissue specification; matter printed in italics indicates the additions made by reissue.

This is a continuation of application Ser. No. 904,662, filed Sep. 8, 1992, now abandoned, which is a continuation-in-part of U.S. application Ser. No. 868,794, filed Apr. 15, 1992, abandoned, which is a continuation-in-part of U.S. Ser. No. 807,446, filed Dec. 13, 1991, abandoned, which is a continuation-in-part of U.S. Ser. No. 365,567, abandoned.

BACKGROUND OF THE INVENTION

1. Field of the Invention

This invention relates to the use of primary human cells as vehicles for human gene transfer. More particularly, this invention relates to the use of human cells (such as, for example, but not limited to, human blood cells) as vehicles for the transfer of human genes encoding therapeutic agents and/or genes encoding detectable markers.

2. Background Information

Retroviral-mediated gene transfer is a new therapeutic approach for the treatment of human disease (W. F. Anderson, Science 226:401 (1984)). Initial attention has centered on candidate diseases affecting the bone marrow such as the hemoglobinopathies and severe combined immunodeficiency. Early attempts at bone marrow gone transfer in large mammals and primates were only partially successful. As an additional approach, specific blood cells, for example lymphocytes, have been used. Lymphocytes have several features which make them potentially attractive cellular vehicles for gene therapy (K. Culver, et al., J. Cellular Biochemistry Suppl. 12B:171 (1988); R. M. Blaese, et al, Clin. Research 37:599A (1989)).

Lymphocytes are readily available from peripheral blood as a single cell suspensions and they are easily manipulated in tissue culture where the availability of recombinant growth-factors such as rIL-2 permits their expansion by thousands of fold. This adaptability to tissue culture allows serial attempts at gene insertion, selection procedures and time to test for gene expression and other properties of the gene-transduced cells prior to their return to the patient. Long-lived antigen-specific memory lymphocytes proliferate when exposed to their appropriate antigen and thus the population of gene-treated lymphocytes can be selectively and specifically expanded in vivo by immunization of the host. Finally, some populations of antigen-specific lymphocytes "target" to sites in the body containing deposits of antigen. Therefore, it is expected that gene-treated antigen-specific lymphocytes can be used to deliver specific gene products directly to the site of pathology, such as a tumor, in a treated patient. For example, clinical studies with systemically administered recombinant cytokines alone and in conjunction with tumor infiltrating lymphocytes of certain cancers (S. A. Rosenberg, et al, New Engl. J. Med. 318:889 (1987); S. A. Rosenberg, et al., J. Natl. Cancer Institute 80:1393–1397 (1988)). It is expected that TIL transduced with genes promoting secretion of such a cytokine and using the TILs wn unique antigen-specific recept rs to target them to deposits f tumor will permit greater antitumor effect with less systemic toxicity.

SUMMARY OF THE INVENTION

In accordance with an aspect of the present invention, there is provided primary human cells which are genetically engineered with DNA (RNA) which encodes a therapeutic agent of interest, and the genetically engineered cells are employed as a therapeutic agent. (The term "therapeutic," as used herein, includes treatment and/or prophylaxis).

A primary cell is one which will not have indefinite growth in culture, i.e., the cells has not been manipulated or transformed to provide for indefinite growth in culture.

The DNA (RNA) which is used for transducing the human cells may be one whose expression product is secreted from the cells. In another embodiment, the DNA (RNA) cures a genetic deficiency of the cells and the expression product is not secreted from the cells (for example, the expression product of DNA encoding ADA is not secreted from the cells).

The human cells may also be genetically engineering with DNA (RNA) which functions as a marker, as hereinafter described in more detail.

Thus, in accordance with another aspect of the present invention, there are provided primary human cells which are genetically engineered to include DNA which encodes a marker or therapeutic, with such cells expressing the encoded product in vivo.

In one embodiment, the invention is directed to a method of enhancing the therapeutic effects of human primary cells. For example, there is provided a method of enhancing the therapeutic effects of human primary cells which specifically "target" to a tissue site in a patient, whereby DNA (RNA) which encodes an agent that enhances the therapeutic effects is inserted in the cells. The tissue site can be, for example, a tumor. The DNA (RNA) produces the agent in the patient's body, and in accordance with such embodiment the agent is expressed at the tissue site itself. Similarly, as hereinabove indicated, primary human cells which are genetically engineered need not be targeted to a specific site and in accordance with the invention, such engineered primary human cells function as a systemic therapeutic; e.g., a desired therapeutic agent can be expressed and secreted from the cells systemically.

In one embodiment, the primary human cells may be primary human nucleated blood cells or primary human tumor cells.

In a preferred embodiment, the primarily human cells are primary human nucleated blood cells.

The primary human blood cell which can be used in the present invention include leukocytes, granulocytes, monocytes, macrophages, lymphocytes, immature forms of each of the previous cells (as well as immature erythroblasts) ($CD_{34}$+cells) and totipotent stem cells.

In one embodiment, human cells, preferably blood cells, which are genetically engineering are cells which are targeted to a specific site; for example, the cells can be tumor infiltrating lymphocytes (TIL cells). In such case, the engineered cells function as a therapeutic at such site. In another aspect, the cells are n t cells which are targeted to a specific site and in such aspect such cells function as a systemic therapeutic.

The DNA carried by the cells can be any DNA having clinical usefulness, for example, any DNA that directly or indirectly enhances the therapeutic effects of the cells. Alternatively, the DNA carried by the cells can be any DNA that allows the cells t exert a therapeutic effect that the cells would not exert. Examples of suitable DNA, which can be used for genetically engineering, f r example, bl od cells, include those that encode cytokines such as tumor necrosis factor (TNF), interleukins (for example, interleukins 1–12), interferons (α,β,γ-interferons). T-cell receptor proteins and the Fc receptors for antigen-binding domains of antibodies, such as immunoglobulins.

In another embodiment, the inserted gases are marker genes which permit determination of the traffic and survival of the transformed cells in vivo. Examples of such maker genes include the neomycin resistance (neoR) gene, multidrug resistant gene, thymidine kinase genes, β-galactosidase, dehydrofolate reductase (DHFR) and chloroamphenicol acetyl transferase.

Thus, in accordance with another embodiment, there is provided a process for treating a patient with a therapeutic agent by providing the patient with primary human cells, preferably nucleated blood cells, genetically engineered with DNA (RNA) encoding such therapeutic agent.

The cells may be genetically engineered in vitro or in vivo. For example, cells may be removed from a patient; genetically engineered in vitro with DNA (RNA) encoding the therapeutic agent, with such genetically engineered cells being readministered to the patient. Such a treating procedure is sometimes referred to as an ex vivo treatment.

Alternatively, DNA (RNA) encoding the therapeutic agent may be administered to the patient for delivery of the DNA in vivo to the targeted cells. Such may be accomplished by the use of a variety of delivery systems, e.g., a retroviral or other viral vector; liposomes etc.

Thus, in accordance with another embodiment, a patient is provided with human primary cells which are genetically engineered with DNA (RNA) encoding a therapeutic agent whereby such therapeutic agent may be expressed in vivo. As hereinabove indicated, such genetically engineered cells may be provided by administering to the patient cells which have been genetically engineered ex vivo or by administering the DNA (RNA) as part of a delivery system for genetically engineering targeted cells in vivo.

In accordance with another embodiment, there are provided primary human cells genetically engineered with DNA (RNA) encoding a therapeutic agent.

In accordance with a further aspect of the present invention, there is provided a composition comprising (i) primary human cells genetically engineered with DNA (RNA) encoding a therapeutic agent and (ii) a pharmaceutically acceptable carrier suitable for administration to a patient. Preferably, the primary human cells are primary human nucleated blood cells. The carrier may be a liquid carrier (for example, a saline solution) or a solid carrier, e.g., an implant. In employing a liquid carrier, the engineered cells may be introduced, e.g., intravenously, subcutaneously, intramuscularly, intraperitoneally, intralesionaly, etc.

DETAILED DESCRIPTION OF THE INVENTION

Figure 1A:
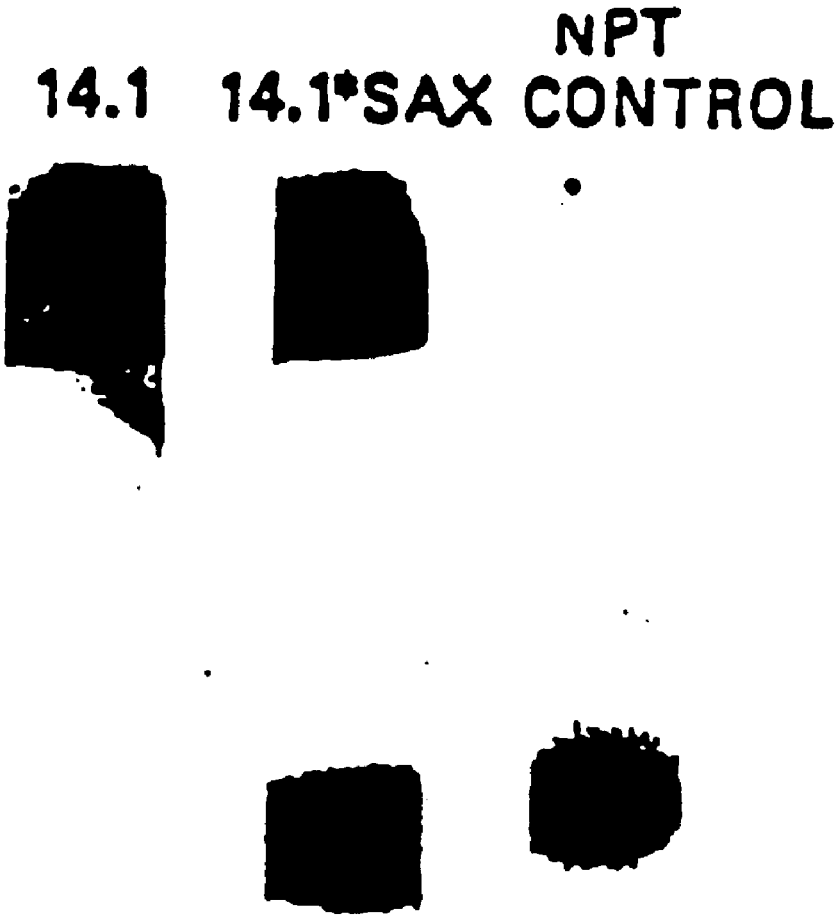
FIG. 1A dem nstrates by assay for functi nal enzyme that murine 14.1-T cells containing an inserted SAX vector express high levels of the neomycin resistant (neoR) gene product, aeomycin phosphotranferase (NPT).

As indicated above, the present invention relates to the use of primary human cells as cellular vehicles for gene transfer. The genes can be any gene having clinical usefulness, for example, therapeutic or marker genes. Preferably, the primary human cells are blood cells. The term "blood cells" as used herein is meant to include all forms of nucleated blood cells as well as progenitors and precursors thereof, as hereinabove described.

In one embodiment, the invention is directed to a method of enhancing the therapeutic effects of human primary cells, preferably blood cells, that are infused in a patient, comprising: (i) inserting into the human primary cells of a patient a DNA (RNA) segment encoding a product that enhances the therapeutic effects of the human primary cells; and (ii) introducing cells resulting from step (1) into the patient. The gene can be inserted into the human primary cells using any gene transfer procedures, for example, retroviral-mediated gene transfer, electroporation, calcium phosphate mediated transfection, microinjection or proteoliposomes. Other vectors can be used besides retroviral vectors, including those derived from DNA viruses and other RNA viruses. As should be apparent when using an RNA virus, such as virus includes RNA which encodes the desired agent, with the human primary cells which are genetically engineered with such RNA virus thus being provided with DNA encoding the agent.

More specifically, there is provided a method of enhancing the therapeutic effects of blood cells, that are infused in a patient, comprising: (i) inserting into the blood cells of a patient a DNA (RNA) segment encoding a product that enhances the therapeutic effects of the blood cells; and (ii) introducing cells resulting from step (i) into the patient under conditions such that the cells resulting from step (i) "target" to a tissue site. In the alternative, as previously described the cells are not "targeted" and function as a systemic therapeutic. The genes are inserted in such a manner that the patient's transformed blood cell will produce the agent in the patient's body. In the case of antigen-specific blood cells which are specific for an antigen present at the tissue site, the specificity of the blood cells f r the antigen is n t lost when the cell produces the product.

Alternatively, as hereinbefore indicated, DNA (RNA) may be inserted into the blood cells of a patient, in vivo, by administering such DNA (RNA) in a vehicle which targets such blood cells.

The method of the invention can-be used, for example, in the treatment of cancer in a human by inserting into human primary cells, such as, f r example, blood cells, which specifically "target" to a tumor and which have been removed from a cancer patient and expanded in culture, genes that enhance the anti-tumor effects of the blood cells. The blood cells can be expanded in number before or after insertion of the genes. The method of gene transfer in the blood cells is as described above. Thus, the procedure is performed in such a manner that upon injection into the patient, the transformed blood cells will produce the agent in the patient's body, preferably at the site of the tumor itself.

The gene carried by the blood cells can be any gene which directly or indirectly enhances the therapeutic effects, of the blood cells. The gene carried by the blood cells can be any gene which allows the blood cells to exert a therapeutic effect that it would not ordinarily have, such as a gene encoding a clotting factor useful in the treatment of hemophilia. The gene can encode one or more products having therapeutic effects. Examples of suitable genes include those that encode cytokines such as TNF, interleukins (interleukins 1–12), interferons (α, β, γ-interferons), T-cell receptor proteins and Fc receptors for antigen-binding domains of antibodies, such as immunoglobulins.

Additional examples of suitable genes include genes that modify blood cells to "target" to a site in the body to which the blood cells would not ordinarily "target," thereby making possible the use of the blood cell's therapeutic properties at that site. In this fashion, blood cells such as TIL can be modified, for example, by introducing a Fab portion of a monoclonal antibody into the cells, thereby enabling the cells to recognize a chosen antigen. Likewise, blood cells having therapeutic properties can be used to target, for example, a tumor, that the blood cells would not normally target to. Other genes useful in cancer therapy can be used to encode chemotactic factors which cause an inflammatory response at a specific site, thereby having a therapeutic effect. Other examples of suitable genes include genes encoding soluble CD4 which is used in the treatment of AIDS and genes encoding α-antitrypsin, which is useful in the treatment of emphysema caused by α-antitrypsin deficiency.

The gene therapy of the present invention is useful in the treatment of a variety of diseases including but not limited to adenosine deaminase deficiency, sickle cell anemia, thalassemia, hemophilia, diabetes, α-antitrypsin deficiency, brain disorders such as Alzheimer's disease, and other illnesses such as growth disorders and heart diseases, for example, those caused by alterations in the way cholesterol is metabolized and defects of the immune system.

In still another embodiment, there is prodded a method of detecting the presence of human primary cells, such as, for example, blood cells containing a marker present in a patient, comprising (i) inserting into human primary cells removed from the patient a DNA (RNA) segment encoding the marker under conditions such that the marker is present in the blood cells; (ii) introducing cells resulting from step (i) into the patient; (iii) removing from the patient an aliquote f tissue (which can be, for example, normal tissue, cancerous tissue, blood, lymph nodes, etc.) including cells resulting from step (ii) and their progeny; and (iv) determining the quantity of the cells resulting from step (ii) and their progeny, in said aliquot.

M re specifically, the present invention comprises a method f detecting the presence f blood cells containing a marker, present at a site in a patient, to which site the blood cells "targets", c mprising (i) inserting into blood cells removed from the patient that are specific for an antigen (either known or unknown) present at the site and that target to site, a DNA segment encoding the marker under conditions such that the marker is present in the blood cells, (ii) introducing cells resulting from step (i) into the patient under conditions such that cells resulting from step (ii) can be found at the site; (iii) removing from the patient an aliquot of tissue from the site, which aliquote includes cells resulting from step (ii) and their progeny; and (iv) determining the quantity of the cells resulting from step (ii) and their progeny, in said aliquot. The marker gene can be, for example, inserted into blood cells which specifically "target" to a tumor in order to determine the traffic and survival of the transformed blood cells in vivo. Alternatively, the transformed blood cells circulate through the body, rather than targeting to a particular tissue site.

The marker gene can be any gene which is different from the genes in the blood cell into which the marker gene is inserted. Examples of such marker genes include neoR, multi-drug resistant gene, thymidine kinase gene, β-galactosidase, dehydrofolate reductase (DHFR) and chloroamphenicol acetyl transferase.

The marker gene can be inserted into a human primary cell, such as a blood cell, together with a therapeutic gene or separately. The marker gene and the therapeutic gene may also be one and the same.

Figure 1B:
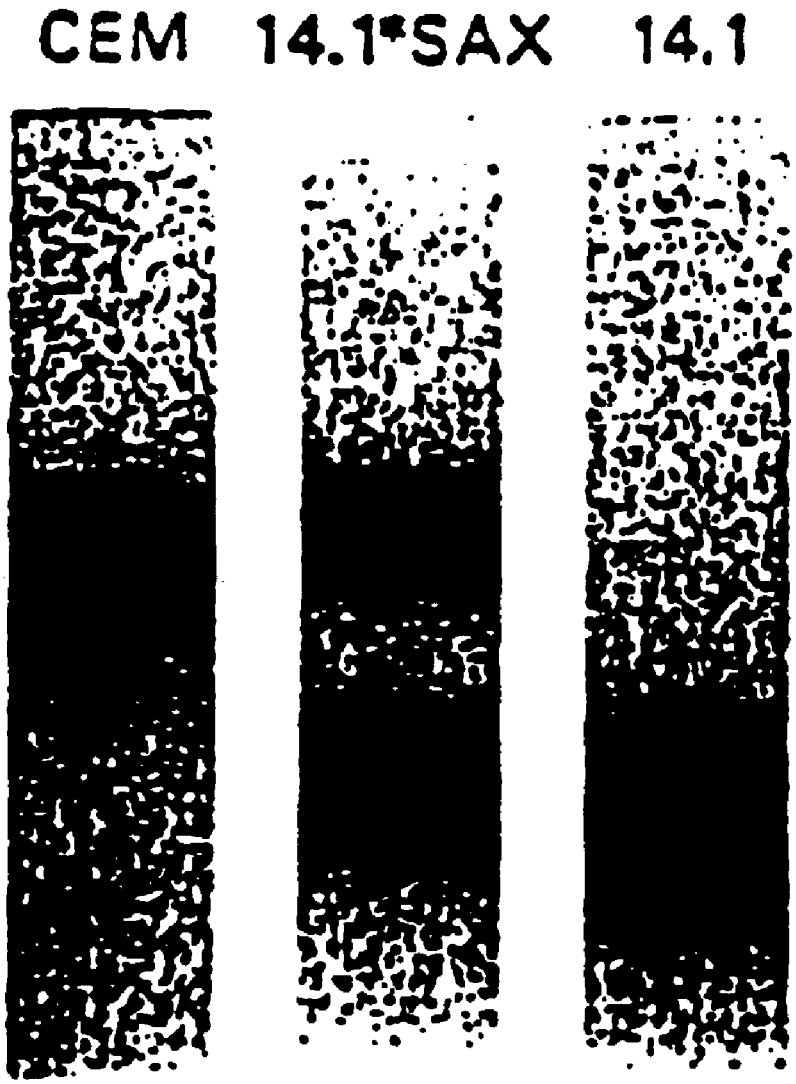
FIG. 1B demonstrates the expression f human adenosine deaminase (hADA), also encoded by the SAX vector inserted in the murine 14.1-T cells.

To initially test the feasibility of using lymphocytes for gene transfer, the retroviral gene transfer vector SAX (P. W. Kantoff, et al, PNAS 83:6563 (1986)) was used to insert the genes for human adenosine deaminase (hADA) and neomycin resistance (neoR) into the murine T cell line 14.1 SAX is a moloney virus based vector with the neoR gene promoted from the retroviral LTR and the hADA gene promoted from an internal SV40 promoter. The 14.1 T cell line was derived from the draining lymph nodes of a BIO.D2 mouse previously immunized with sperm whale myoglobin (SWM) by repeated cycles of antigen stimulation of these lymphocytes in tissue culture (I. Berkower, et al., J. Immunol. 135:2628 (1985)). These 14.1 T-cells proliferate when challenged with SWM in the presence of histocompatible antigen-presenting cells (without exogenous IL-2) or when stimulated with PHA and rIL-2 in vitro. An average of 20% of the 14.1-T cells achieved stable insertion of the SAX vector after a supernatant infection protocol (P. W. Kantoff, et al, PNAS 83:6563 (1986)). The population of SAX-transduced 14.1-T cells was selected in the neomycin analog G418 so that all cells were expressing the introduced genes and were then expanded by repeated cycles of antigen stimulation to obtain large numbers of transduced cells. FIG. 1A demonstrates by assay for functional enzyme that the cells containing the inserted SAX vector are expressing high levels of the neoR gene product, neomycin phosph transferase (NPT). FIG. 1B demonstrates expression of human adenosine deaminase (hADA), also encoded by the SAX vector inserted in these T cells. The SAX-transduced, expanded population of 14.1 cells (14.1SAX) were functionally unchanged except f r the gene insertion and its expressi n which provides for G418 resistance, the cells remained responsive to SWM in vitro.

A thymic nude mice were then injected intraperitoneally with $20\times10^6$ 14.1SAX T-cells and immunized with 100 μg soluble SWM. Athymic recipients were chosen for these experiments because they have very little endogenous Te cell activity and therefore any T cells recovered from these mice at a later date should represent the original injected 14.1 SAX cells or their progeny.

Figure 2:
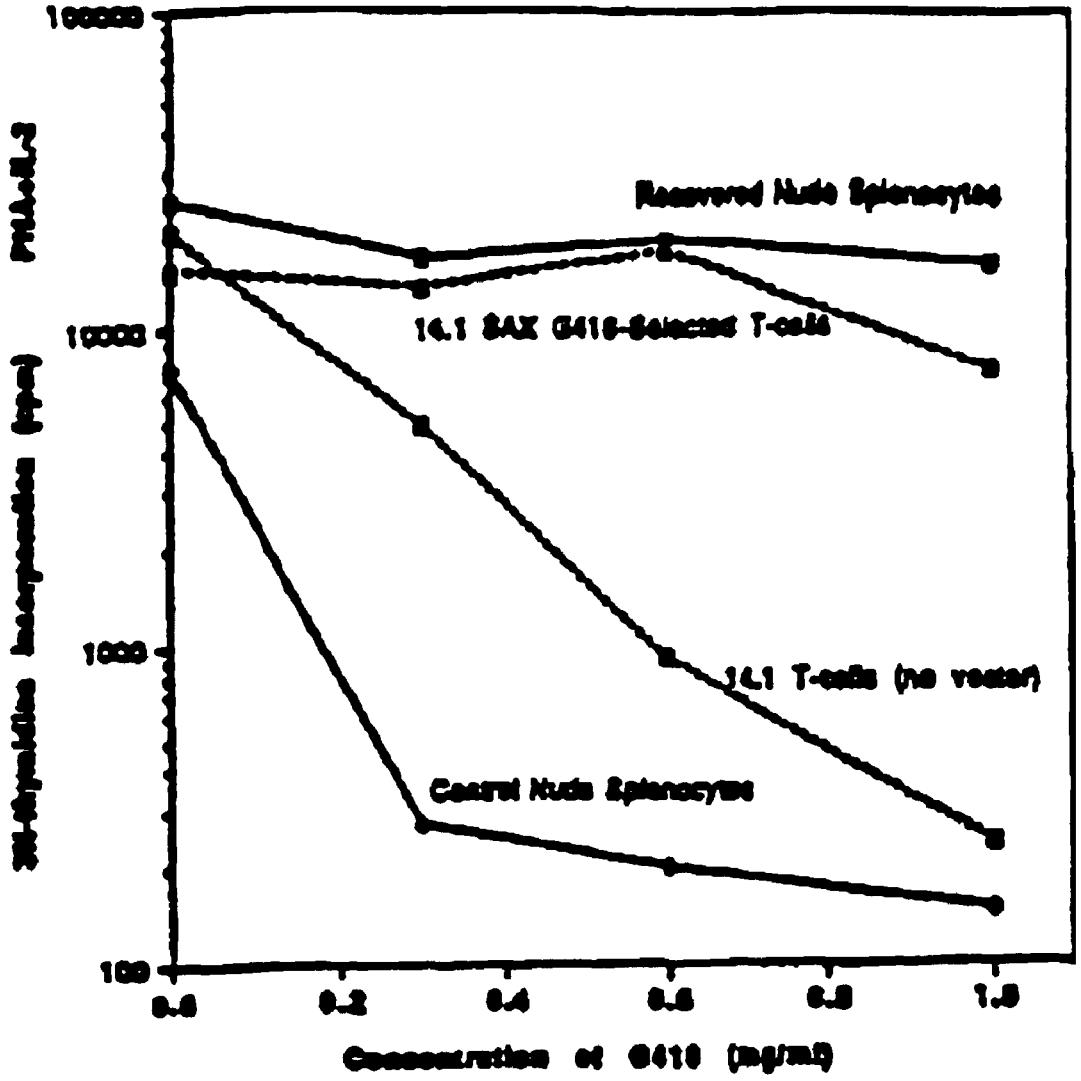
FIG. 2 shows the proliferative response of murine splenic lymphocytes and 14.1-T cells to stimulation with phytohemagglutinin and IL-2and the effect of G418 on this proliferati n.

Thirty-seven days after intraperitoneal injection of the 14.1SAX-T cells, spleens from recipient athymic mice were removed and tested to determine if any cells expressing the introduced genes could be detected by demonstrating G418 resistance and hADA. FIG. 2 shows the proliferative response of splenic lymphocytes and 14.1 cells to stimulation with phytohemagglutinin and IL-2 and the effect of G418 on this proliferation. While control nude mouse splenocytes did proliferate modesty to PHA+IL-2, this response was abolished by low concentrations of G418. By contrast, PHA and IL-2 responsive lymphocytes recovered from the spleens of nude mice injected with 14.1SAX-T cells 37 days earlier remained resistant to G418, indicating persistence of the transferred 14.1 cells as well as continued expression of the introduced neoR gene. These G418-resistant recovered T cells were further expanded in IL-2, tested for expression of the hADA isozymes by cellulose acetate electrophoresis and were found to be expressing the product of this introduced gene as well. Thus, antigen-specific T cells maintained in tissue culture and transduced with foreign genes by retroviral-mediated gene transfer were able to survive and express the introduced genes for at least 37 days when reinjected into an intact host animal.

Because of the success in demonstrating that cultured T lymphocytes carrying inserted foreign genes could survive for prolonged periods of time in mice and continue to express the inserted genes, situations were investigated where the technique might be used in mass. S. A. Rosenberg, et al, Science 223:1318 (1986) have shown that the treatment of experimental cancer with T lymphocytes which have been isolated directly from the tumor and expanded in culture with rIL-2 can cause tumor regression . Techniques for growing the tumor infiltrating lymphocytes (TIL) from human cancers have been developed and the functional and phenotypic properties of these cells have been extremely characterized (L. M. Muul, et al, J. Immunol. 138:989 (1987); S, Topalian et al, J. Immunol. Meth. 102:127 (1987); A. Belldegrum, et al, Cancer Res. 48:206 (1988)). In the initial clinical studies using human TIL along with intravenous infusion of rIL-2 in 20 patients with advanced metastatic melanoma, objective remissions with at least 50% reduction of tumor burden were seen in 55% of the patients (S. A. Rosenberg et al, N. Engl. J. Med. 319:1676 (1988)). These were patients who had failed air conventional forms of cancer treatment and thus TIL therapy is expected to open a significant new direction in the treatment of cancer.

At this state in the development of TIL therapy, many issues remain to be clarified including a more complete understanding of the features of individual TIL preparations which correlate with clinical antitum r effects, the in vivo distribution and time of persistence f TTL after infusion, and whether distinct TIL functional phenotypes localize in the body in ways which will permit prediction of their clinical efficacy.

Trafficking studies using radionuclides as cell labels have shown that TIL from some patents do appear to specifically accumulate in areas of tumor within the first few days, alth ugh these studies have been limited by the short half-life of the clinically acceptable isotopes (2.8 days for In) and the high rate f spontaneous release of the isotope from the TIL (B. Fisher, et al, J. Clin. Oncol. 7:250 (1989)). Genes used as labels could potentially solve several of the problems associated with radionucleotide labels. Genes become stably integrated into the genome of the target cell and then will be completely destroyed when the cell dies so that any detected label should only be associated with the original marked cell or its progeny. In contrast to radionuclide tags which become diluted as cell proliferate, a gene label will also equally mark progeny cells derived by continued proliferation of the originally labelled cell population as occurs when TIL proliferation is driven by IL-2 infusions given to the patient. An important characteristic that is unique to the use of genes as cell labels in their ability to introduce an entirely new functional property to the target cell. With the gene neoR, for example, the target cell acquires resistance to the neomycin analog G418 which permits, as we have shown for mouse 14.1SAXT-cells, the selective recovery of the gene-marked cells by regrowth of recovered cells in the presence of G418. With recovery, the cells from different sites could then be analyzed for their functional phenotypes and potential correlations with clinical efficacy.

To explore the possibility that inserted genes might be used to label TIL, cultured TIL from 6 patients with metastatic malignant melanoma were studied using the retroviral vector N2, which vector was described by (D. Armentano, et al, J. Virology 61:1647 (1987)). N2 contains the gene neoR promoted by the retroviral LTR and has been used extensively by the inventors in studies of bone marrow gene-transfer in mide and primates during the past 5 years (M. E. Egitis, et al, Science 230:1396 (1985); D. Kohn, et al, Blood Cells 13:285–298 (1987)); P. W. Kantoff, et al, J. Exp. Med. 166:219 (1987)). Human TIL were efficiently transduced with N2 by exposure to viral supernatant produced by the amphotrophic packaging cell line PA317 which package cell line was described by (A. D. Miller, et al, Molecular Cellular Biol. 6:2895 (1986)). The N2-transduced TIL expressed sufficient neomycin phosphotransferase (NPT) to become resistant to the toxic effects of G418 on cellular proliferation as demonstrated in FIG. 3A. On average, 10–15% of the N2-treated TIL population grew in G418 while >99% of the untreated TIL died. After 10 days of selection in 0.3 mg/ml G418, the surviving N2-treated population was G418 resistant. FIG. 3B shows growth curves of N2-transduced and untreated TIL for the 30 day period following gene insertion. Growth of the N2-transduced TIL population as a whole slows initially when G418 is added to the culture (not shown, but resumes exponential expansion as growth of the NeoR-expressing G418-resistant subpopulation becomes established. After completion of selection, the N2-transduced cells as a rule grew at a rate comparable to that of TIL not transduced with the neoR gene.

To further characterize these cells and to study possible differences between th gene-transduced and non-transduced TIL, studies of the cell membrane phenotype and the constitutive cytotoxic properties f the tw cell rpus have been performed (see Table 1 below).

TABLE 1

CHARACTERISTICS OF N2-TRANSDUCED AND NON-TRANSDUCED TIL

| | Untreated TIL | | | | N2-transduced and G418 Selected | | | |
|---|---|---|---|---|---|---|---|---|
| | Phenotype % Positive | | Cytotoxicity % $^{56}$Cr Release | | Phenotype % Positive | | Cytotoxicity % $^{56}$Cr Release | |
| Patient | CD4 | CD8 | Auto | NK | CD4 | CD8 | Auto | NK |
| 1 | 0 | 97.9 | 0 | 0 | 0 | 98.7 | 0 | 0 |
| 2 | 81.8 | 3.9 | 0 | 0 | 88.6 | 1.4 | 0 | 0 |
| 3 | 30.7 | 60.5 | 26.4 | 0 | 6.9 | 82.2 | 26.1 | 4.7 |
| 4 | 76.5 | 13.7 | 0 | 0 | 30.5 | 68.6 | 0 | 0 |
| 5 | 0.1 | 97.7 | 22.5 | 0 | 0.7 | 98.2 | 25.5 | 0 |
| 6 | 8.9 | 94.7 | 4 | 0 | 5.4 | 95.0 | 2 | 0 |

TIL transduced with N2 and selected with 0.3 mg/ml G418 for 10–14 days were compared with non-transduced TIL from 6 patients with methastatic malignant melanoma. These populations were analyzed for their surface membrane phenotype as revealed by FACS analysis of $1\times10^6$ TIL stained monoclonal antibodies. Antibodies to CD4(Leu 3) and CD8 (Leu 2) were used on populations and the percentage of the cells positive for each determinant are shown.

Constitutive cytotoxic function of each TIL population was determined for autologous tumor targets (auto) and the NK sensitive target K562 (NK) as well as for allogeneic tumor and sensitive target cells (not shown) by a standard 4 hour $^{56}$Cr release assay at E:T ratios of 40:1, 15:1, and 4.5:1. Data shows target lysis at the 40:1 E:T ratio. TIL isolated from different individual donors have different phenotypic profiles as determined by various cell membrane determinants (CD4, CD8, etc.) and different levels of cytotoxic activity toward autologous tumor and other target cell types. Human TIL of both major phenotypic subgroups (CD4 and CD8) were readily transduced by the N2 vector and expressed G418 resistance. Some transduced and selected TIL populations (patients 3 and 4) showed more drift in their phenotypic composition than others, and as expected with more prolonged culture, all of the TIL populations became progressively oligoclonal whether or not they had been transduced with N2 (not shown). TIL are often cytolytic for autologous tumor cells but not other target cell types in vitro. Of this group of six patients, TIL isolated from two were cytolytic to autologous tumor cells, but not alleogeneic melanoma tumor cells, NK (K562) or LAK (Daudi) sensitive targets. The functional cytotoxic activity profile of the TIL was unaffected by N2 transduction and G418 selection, even in those TIL populations showing some drift in T cell subset composition measured by surface membrane antigen phenotype.

The present invention will be illustrated in detail in the following examples. These examples are included for illustrative purposes and should not be considered to limit the present invention.

EXAMPLE 1

The following experiment demonstrates that murine 14.1-T cells containing an inserted SAX vector express high levels of the neoR gene product, NPT, as well as expressing hADA.

Long term cultures of the murine T cell line 14.1 were maintained by repeated cycles of stimulation with 4.0 μM SWM in the presence of fresh irradiated (3000 R) B10.D2 spleen cells as antigen-presenting cells. Four days after antigen stimulation, the cultures were fed with complete fresh medium and placed n irradiated syngeneic spleen cells f r a 10 day rest phase. No ex gen us IL-2 was used with this T cell line. T introduce ex genous genes int these 14.1-T cells, 3 days after antigen stimulation the proliferating activated 14.1 cells were exposed to SAX supernatant (MOI=5) in the presence of 8 μg/ml polybrene for two sequential 4 hour incubation.

Twenty-four hours later the SAX-transdermal 14.1 cells were placed under selection with 0.3 mg/ml G418 for 14 days. The SAX-transduced G418 selected cells were then expanded by repeated 14 day cycles of antigen stimulation and rest on syngeneic feeder cells. Lysates from the G418-selected 14.1 population were prepared and assayed for the presence of NPT by measuring the phosphorylation of kanamycin with P32 labelled ATP after separation of NPT from endogenous phosphotransferases on a non-denaturing polyacrylamide gel (B. Reiss, et al, Gene 30:211 (1984)).

As shown in FIG. 1A, the 14.1 cells containing the inserted SAX vector expresses high levels of NPT.

Lysates of the 14.1 cells were separated by electrophoresis on cellulose acetate (B. Lira, et al, Molecular Cellular Biol. 7:3459 (1987)) which was then stained for the presence of the murine and human isozymes of ADA (FIG. 1B). The human T cell line CEM was included as a control for the migration of hADA.

The results are shown in FIG. 1B which demonstrates the expression of hADA.

EXAMPLE 2

The following experiment was performed in order to demonstrate the continued expression of a transferred gene in gene modified T-cells. Specifically, the effect of G418 on the proliferative response of murine splenic lymphocytes and 14.1-T cells to stimulation with phytohemagglutinin and IL-2 was studied.

Cultures of 14.1-T cells, 14.1SAX transduced T cells, splenic lymphocytes from nude mice and splenic lymphocytes recovered from nude mice that had been given an intraperitioneal injection of $20\times10^6$14.1SAX T cells 37 days earlier were established with $2\times10^5$ cells/ml in flat bottom microculture trays using medium and culture conditions previously described (L. Berkower, et al, J. Immunol. 135:2628 (1985) Proliferation in response to stimulation with 5 μg/ml PHA (Wellcome) and 100 n/ml rIL-2(Cetus Corporation) was measured as the incorporation of 3H thymidine into cellular DNA following an overnight pulse with 0.4 μCl added after 72 hours of culture. G418 prepared as the concentrations of active drug indicated (FIG. 2) was added at the initiation of culture. Cultures were harvested for scintillation counting using a Sakron TM cell harvesting system.

FIG. 2 shows, as the mean of triplicate cultures, the proliferative response of the murine splenic lymphocytes and 14.1-T cells to stimulation with phytohemaglutimin and IL-2 and the effect on G418 on this proliferation. A review of the figure shows that while control nude in use splenic lymphocytes proliferated modestly to PHA+IL-2, this response was abolished by low concentrati ns of G418. By contrast, PHA and IL-2 responsively lymphocytes recovered from the spleens of nude mice injected with 14.1SAX-T cells 37 days earlier remained resistant to G418, indicating persistence of the transferred 14.1 cells as well as continued expression of the introduced neoR gene.

EXAMPLE 3

The experiment described bel w was perf rmed in order to verify that human N2-transduced TIL expresses sufficient NPT to become resistant to the toxic effects of G418 on cellular proliferation.

TIL grows from a tumor biopsy obtained from a patient with metastatic malignant melanoma were exposed to two sequential 4 hour exposure to N2 supernatant (average viral titer $10^6$/ml, MOI=2) in the presence of 5 μg/ml protamine sulfate (K. Kornetta, et al, J. Viorol. Meth. 23:187 (1989)). Twenty-four hours later an aliquot was removed and placed under selection in 0.3 mg/ml G418 for 10 days. The cells were then to grown without G418 for two weeks and then were tested for the effect of various concentrations of G418 on their proliferative response to 1000 u/ml IL-2.

The untreated TIL (no vector) was compared with TIL which had been transduced with N2 and selected with G418 (N2+G418) and with an N2-transduced TIL population which had not been further selected in G418 (N2). Proliferative was measured by 3H-thymidine incorporation as described in Example 2.

Figure 3A:
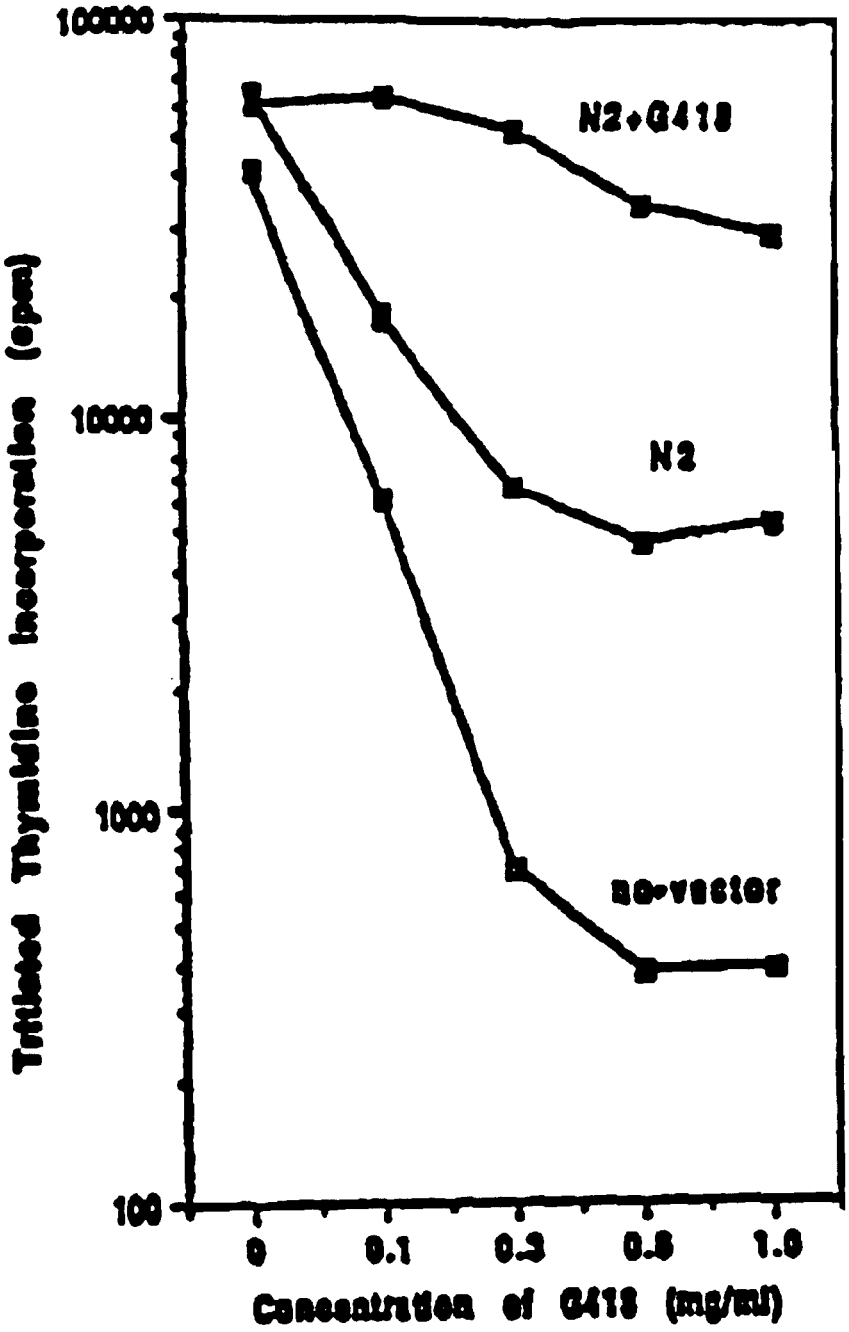
FIG. 3A demonstrates that human N2-transduced TIL expresses sufficient NPT to become resistant to the toxic effects of G418 on cellular proliferation.
Figure 3B:
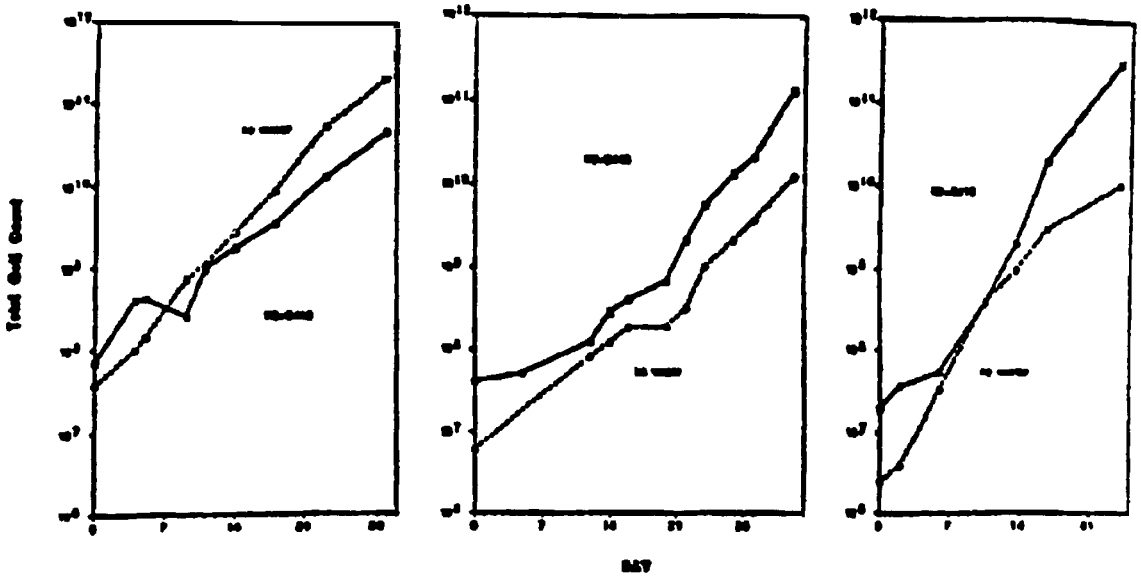
FIG. 3B shows growth curves of human N2-transduced and untreated TIL for the 30 day period following gene insertions.

The results are shown in FIG. 3A, wherein it may be seen that, on average, 10–15% of the N2-treated TIL population grew in G418 while >99% of the untreated TIL died After 10 days of selection in 0.3 mg/ml G418, the surviving N2 treated population was G418 resistant.

FIG. 3B shows the growth curves of the N2-transduced and the untreated TIL for the 30 day period following gene insertion. These results were obtained using the following procedure.

TIL from patent 1 were grown from a tumor biopsy as described (Tobalian et al, J. Immune Method 138:4006–4011 (1987)) and then an aliquot was transduced with the N2 vector by two 4-hour exposures to viral supernatant (note: LNL 6 is identical to N2 except that LNL6 has several additional safety features). Forty-eight hours later the transduced population was placed under selection for 10 days with 0.3 mg/ml G418. Non-transduced TIL exposed to this selection protocol were all dead by day 10. Growth of the N2-transduced TIL population allowed when placed in G418, but resumed at an exponential rate while still under selection as the cells expressing the neoR gene became dominant by day 10. TIL cultures were fed and split as required (1–2 times per week) and the cumulative cell total calculated when the running total reached $>10^6$ cells to that larger numbers of cells would not have to be maintained in culture.

In this example, about 15% of the N2 - treated TIL population expressed the inserted gene sufficiently to permit growth in 0.3 mg/ml G418. After completion of selection, the N2-transduced cells at a rule grew at a rate comparable to that of TIL not transduced with the neoR gene.

EXAMPLE 4—GENE MODIFIED T-CELL CLINICAL PROTOCOL

The TNF-NeoR vector is constructed by modifying the Monkey murine leukemia vector.

Construction f TNF vector

The TNF gene containing water, LT125N, was constructed from the vector LXSN (Miller AD and Rossman G., 1989, Biotechniques 7:980–990.), usign the entire 233 amino acid sequence encoding cDNA f the natural TNF genes (Pennies, et al, 1984, Nature 312, 724–729, Wang, et al, Science 228, 149–154). The ribosome binding site used upstread of the TNF gene was a syntehtic one, a consensus sequence f r translation initiation based on Kozak's rules (Kozak, Nucle. Acids Res. 12, 857–872 (1984) and having the nucleotide sequence 5' TTCCGCAGCAGCCCGC-CACC3'. The vectors construct was packaged using the PA317 packaging cell line (Miller et al., Mol. Cell Biol. 6, 2895–2902 (1986)).

Retroviral vector supernatant is produced by harvesting the cell culture medium from the PA317 packaging line developed by Dr. A. Dusty Miller. This line has been extensively characterized and was used by us in our previous studies of the infusion of TIL modified by the N2 vector. The TNF-Neo vector preparations from PA317 are extensively tested to assure that no detectable replication competent virus is present. Tests for replication-competent virus are conducted on both the vector supernatant and on the TIL after transduction. The follwoing tests are run on the producer line and/or the viral supernatant:

1) The viral titer is determined on 3T3 cells. Viral preparations with titers greater than $5\times10^4$ colony forming units/ml are used.

2) Southern blots are run on the producer line to detect the TNF gene.

3) TNF production by the product line is measured and should be significantly above baseline control values. TNF is assayed using standard biologic assays on the L929 amino cell line (Asher et al. J. Immunol 138:963–974, 1987) or by ELISA assay (R&D Systems, Minneapolis, Minn.).

4) Sterility of the producer line and the supernatant is assured by testing for aerobic and anaerobic bacteria, fungus and for mycoplasma.

5) Viral testing is performed including:

a. MAP test b. LCM virus c. Thymic agent d. S+L—assay for ecotropic virus e. S+L—for xenotropic virus.

f. S+L—for amphotropic virus.

g. 3T3 amplification.

6) Electron microscopy is performed to assure the absence of adventitions agents.

Following transduction and growth of the TIL population the following tests are performed on the TIL prior to infusion into patients.

1) Cell viability is greater than 70% as tested by trypan blue dye exclusion.

2) Cytologic analysis is performed on over 200 cells prior to infusion to assure that tumor cells are absent.

3) Sterility is assured by testing for aerobic anaerobic bacteria, fungus and mycoplasma.

4) S+L—assay including 3T3 amplification must be negative.

5) PCR assay for the absence of 4070A envelope gene must be negative.

6) Reverse transcriptase assay must be negative.

7) S uthern blots run on the transduced TIL to assure that intact provirus is present.

8) TNF protein assay to assure the production of TNF. Cells must be producing at least 100 pg TNF/$10^6$ cells/24 hours.

9) IL-2 will be withdrawn from the culture medium of an aliqu t f r at least one week to assure that cells do n t exhibit auton mous growth in the absence f IL-2.

10) Cyt toxicity against the autol gous and at least tw other targets are tested. The phenotype of the cells as tested by fluorescence activated cell sorting analysis.

At least tw days prior to surgery, peripheral blood lymphocytes are collected by leukapheresis for four hours. These are Ficoll-Hypaque separated and the mononuclear cells from the interface, washed in saline, and placed in culture in roller bottles at $10^6$ cells/ml. Half are placed into AIM-V (a serum free medium, Gibco Laboratories) with 6000 IU/ml IL-2 (Cetus), and Half are placed into RPMI supplemented with 2% type-compatible human serum, penicillin (unless the patient is allergic), gentamicin, and 600 IU/ml IL-2. After 3 to 4days cells are centrifuged and the supernatants are collected and filtered. These are referred to as LAK supernatants.

Immediately upon tumor resection, the specimen(s) is transported to the laboratory in a sterile container and placed on a sterile dissection board in a laminar flow hood. A small reprensentative portion is taken for pathologic analysis, and the rest is minced into pieces roughly 4 mm in diameter. These are placed into an enzyme solution of collagenase, DNAse type I, and hyaluronidase type V for overnight digestion at room temperature. The resulting suspension is filtered through a wire mesh to remove any large debris, washed in saline, and placed on Ficoll-Hypaque gradients. The interface containing viable lymphocytes and tumor cells is collected and washed in saline, and a portion is frozen for subsequent use as targets.

TIL cultures are initiated at $5\times10^5$ ml viable cells (tumor plus lymphocytes) in 80% fresh medium/20% LAK supernatants. For half the cells, the fresh medium is AIM-V supplemented with penicillin, fungizone, and 6000 IU/ml IL-2; for the other half, the fresh medium is RPMI supplemented with 10% human serum, penicillin, gentamicin, fungizone, and 6000 IU/ml IL-2. The cultures are placed into 6-well tissue culture dishes and incubated at 37° in humidified incubators with 5% $CO_2$.

Usually the lymphocyte density is not much increased at the end of seven days in culture, and the cultures are collected, centrifugal, and resuspended at $5\times10^5$ total viable cells/ml in newly prepared 80%/20% medium mixtures of the same type. Occasionally a culture will have increased lymphocyte density and need medium replenishment prior to seven days. After this first passage, TIL are subcultured by dilution when the density is between $1.5\times10^6$ and $2.5\times10^6$ cells per ml; densities of subcultures are established between $3\times10^5$ and $6\times10^5$ ml. Cultures are kept in 6-well dishes when the volume is less than 1 liter, and transferred to 3 liter polyolefins bags (Fenwall) when the volume reaches one liter. The subculture from bags are accomplished with Fluid Fill/Weight Units (Fenwall), which are programmed to pump prescribed weights of TIL culture and fresh medium into a new bag. When subculture volumes exceed 3 liters, the fresh medium used in AIM-5. Cultures growing in serum-containing medium are thus diluted into AIMW, and no further LAK supernatant is added to cultures growing in serum-containing or serum-free medium.

Tumor-infiltrating lymphocytes are transduced when the total number of lymphocytes is about $1–5\times10^8$ or higher. Up t one-half f the TIL culture is centrifuged, the medium is saved, and the cells are resuspended in Viral Supernatant with 5 ug/ml protamine. Multiplicities of infection are about 1.5 to 10. The cells in Vital Supernatant are placed int 800 ml tissue culture flasks at 200 ml/flask and incubated at 37° f r 2 hours. During incubati n, the flasks are agitated every 15 minutes to resuspend the cells. The original medium is centrifuged to remove any remaining cells and decanted into new containers. At the end of 2 hours, the cells are centrifuged and resuspended in the original cleared medium. If the density is such that subculturing is necessary, the cells are diluted slightly to a density of about $10^6$/ml and placed into fresh 6-well tissue dishes for continued incubation. The following day, the above transduction procedure is repeated. If the cell density at the conclusion of this second transduction is such that subculturing is necessary, the cells are diluted to $5\times10^5$/ml for continued incubation.

When TIL are to be selected to G418, the TIL are cultured for 3 to 5 days after the second transduction and then G418 is added directly to the culture bags to a final concentration of 300 ug/ml G418. After 10 to 20 days the cells are washed and resuspended at 3 to $6\times10^5$ cells/ml in fresh medium not containing G418 and then cultured as described above.

When the total TILs for a patient are ready for harvest, $5\times10^6$ cells are taken for cytological examination. Cytospins are examined for the presence of remaining tumor. At least 200 cells are studied and therapy proceeds only when no tumor cells are found. Other TIL samples are taken for characterization of cells surface markers and for assessment of cytotoxicity. Briefly, TILs are stained with fluorescent-labeled antibodies (Leu2, Leu3, Leu4, Lue7, Leu11, Leu15, Leu19, LeuM3, HLADR, and Tac). Chromium release assays are performed with K562, Daudi, autologous tumor, and allogeneic tumor targets.

When the total cell number reaches about $2\times10^{11}$ cells the TILs are collected in two or more batches by continuous flow centrifugation. Some of the TILs are then cryopreserved for future use in $10^{10}$ cell aliquots.

For infusion TIL are reharvested. At the time of cell collection, one liter of saline for injection is pumped through the collection chamber and the centrifuge is stopped. TILs are resuspended in the collection bag, the centrifuge is started again, and another liter of saline is pumped through to fully wash the TILs free of tissue culture medium components. The cells are then filtered through a platelet administration set into 600 ml transfer packs (Fenwall) and 50 ml of 25% albumin and 450,000 IU of IL-2 are added to the 200 to 300 ml volume of cells in saline. The TIL are infused over 30 to 60 minutes through a central venous catheter.

Patients receive either LNL-6 modified TIL or TNF-modified TIL (TNF-TIL).

EXAMPLE 5 ADA CLINICAL PROTOCOL

Fresh peripheral blood mononuclear cells (MNCS) are separated from the red cells and neutrophils by Ficoll-Hypaque density gradient centrifugation. The MNCs are then washed, counted and cultured at approximately $1\times10^6$ cells/well in 24-well tissue culture plates in AIM-V which consists of AIM-V (GIBCO) with 2 mM glutamine, 50 U/ml penicillin, 50 μg/ml streptomycin, 2.5 μg/ml Fungizone and 25–1,000 U/ml f IL-2 (Cetus). At the initial plating, 10 ng/ml OKT3 (Ortho) monoclonal antibody is added to each well. The cells are cultured at 37° C. in a humidified incubator with 5% CO.

Growth, Transduction and Selection of ADA-Deficient T Lymphocytes

Once the T lymphocytes have begun to proliferate (usually 24–96 hr after initial n at the culture) the cells are transduced by use of LASN vector (Blood, V L 72(2) pages 876–81) 2 ml. LASN vector-containing supernatant (contianing protamine 5–10 μg/ml and up to 1,000 U/ml IL-2) are added to the wells after aspirating off the top half of the medium. This is repeated 1–2 times daily for a period of up to 7 days. After the final exposure to retroviral vector the cells are fed with fresh AIM-V and cultured another 2–7 days to permit the cultures to return to exponential growth. Approximately 80% of the culture $0.1–2.5\times10^{10}$ T cells are infused into the patient and the remaining cells cryopreserved for future use or returned to culture for studying growth and selection procedures, phenotype analysis, T cell repertoire analysis and percentage of cells demonstrating vector integration.

An aliquot of the cells infused into the patient is saved for subsequent Southern analysis on the DNA from the cultured cells after digestion with a restriction endonuclease which does not cut within the vector sequence to determine whether the gene-modified cells are polyclonal with respect to retroviral insertion.

Reinfusion of hADA Transduced T Lymphocytes

The transduced cells are harvested, washed, and resuspended in normal saline. The final cell preparation is filtered through a platelet filter and transferred into a syrinige or transfusion pack for infusion. A test dose of 5% of the total volume is infused by peripheral vein followed by an observation period of 5–10 min.

Figure 4:
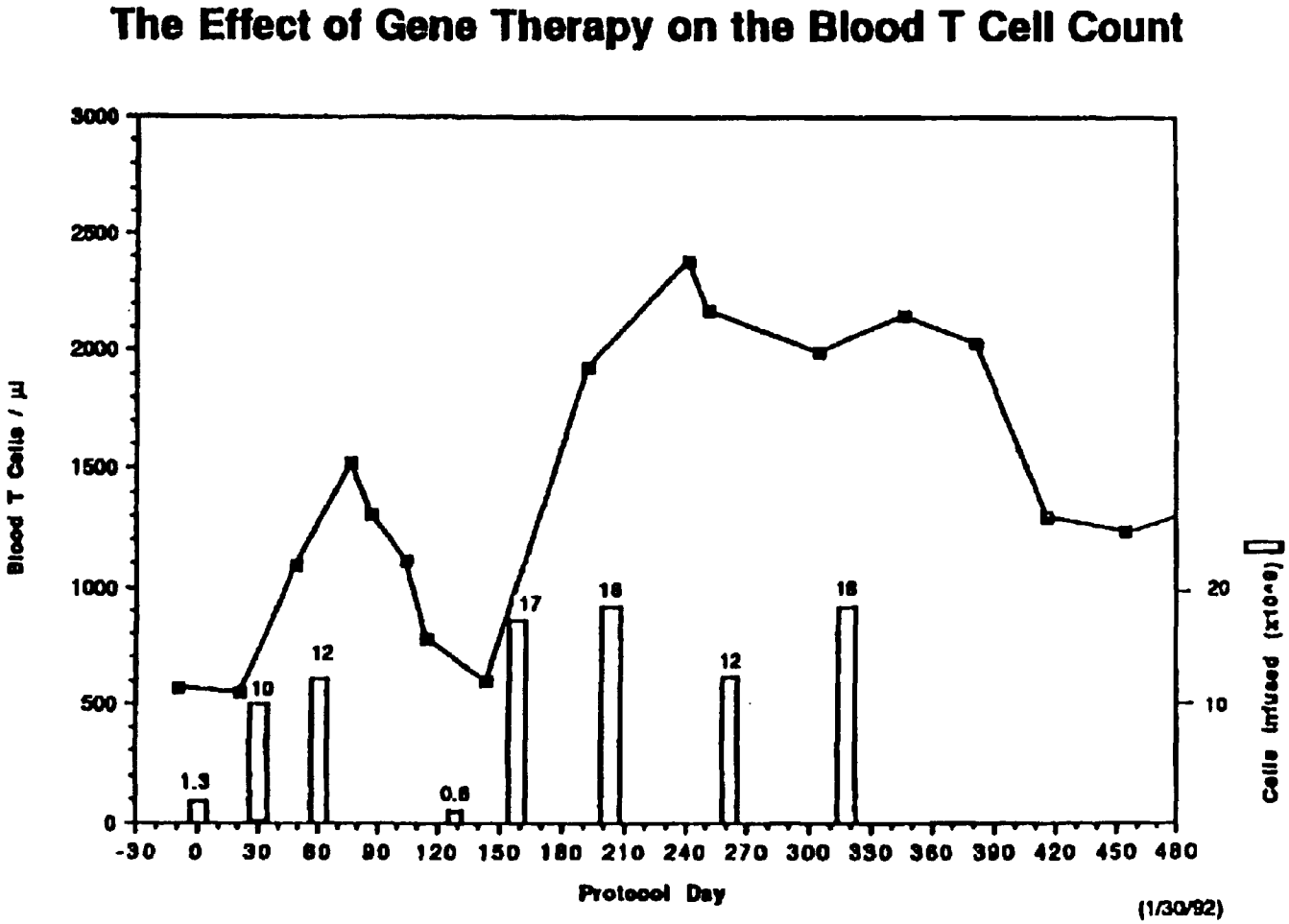
FIG. 4 demonstrates absolute Blood T Cell levels of patient #1 receiving ADA gene therapy in accordance with the procedure of Example 4. The bar portion of the figure is the transduced T-cells infused at the day indicated.
Figure 5:
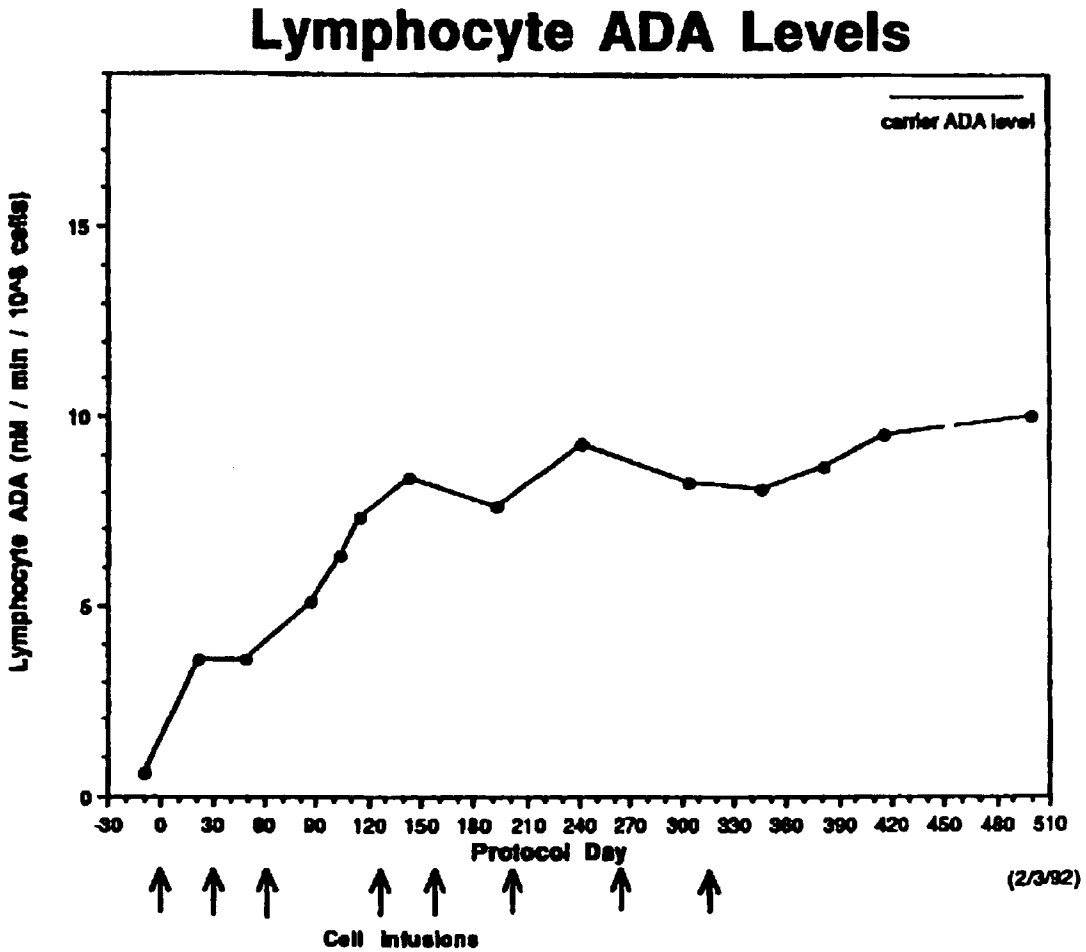
FIG. 5 demonstrates the ADA enzyme activity of patient #1 during treatment.

Transduced cells were administered to patient #1 in the amounts and at the times shown in FIG. 4. The ADA enzyme levels of patient #1 are shown in FIG. 5.

For purposes of completing this disclosure, the entire contents of the references cited herein are hereby incorporated by references and relied upon.

EXAMPLE 6 GENE-MODIFIED TUMOR CELL CLINICAL PROTOCOL

The TNF-NeoR vector was constructed as in Example 4, and retroviral vector supernatant is prepared and tested as disclosed therein.

A. Preparation of Gene-Modified Tumor Cells.

Tumor cell lines are established in tissue culture from tumor fragments or single cell suspensions using standard tissue culture techniques. (Topalian, et al., J. Immunol, Vol. 144, pgs. 4487–4495 (1990)). Tumor and normal tissue are obtained immediately after surgery.

The tumors were minced into 1 $mm^3$ fragments and dissociated with agitation in serum free DMEM (Dulbecco Modified Eagle Medium)(Bio-fluids) containing 2 mM glutamine, 0.1 mg/ml hyaluronidase, 0.01 mg/ml DNase I an d0.1 mg/ml collagenase for 3 hours at room temperature. The cell suspension was then centrifuged at 800 g for 5 minutes and the pellet resuspended in a culture medium consisting of 5 ml of DMEM high glucose (4.5 g/l) with penicillin and glutamine supplemented with 10% fetal calf serum. The cells were either centrifuged prior to being frozen in 90% FCS, 10% DMSO at −80° C., or plated in appropriate dishes or culture flasks in culture medium. Plated cells were incubated at 37° C. in a humidified atmosphere of 5% $CO_2$ and 95% air. Within 48 hrs, the culture medium was changed in order to remove all non-attached material. Subsequently, cultures were incubated for a period of 6 to 8 days without medium change. The tum rs grow as adherent monolayers in tissue culture flasks (Falcon #3028; 175 $cm^{-2}$; 750 ml) containing about 50 ml of medium. When the cells are actively growing and not yet confluent the medium will be poured off and 30–50 ml of medium containing the retroviral supernatant with 5 μg/ml protamine will be added to the flask. Cornetta, et al., J. Virol. Meth., Vol. 23, Pgs. 186–194 (1989). The flasks will be incubated at 37° C. for six hours at which time the medium will be changed. This procedures will be repeated up to three times. After 24 to 48 hours medium containing 300 μg/ml G418 is added directly to the flask and the ells will be grown and subcultured for 7 to 14 days in G418 containing medium. The G418 concentrations may be raised to 1 mg/ml depending on the health of the culture.

B. Tests on the Transduced Tumor Population.

The following tests are performed on the tumor cells prior to injection into patients.

1) Call viability will be greater than 70% as tested by trypan dye exclusion.

2) Sterility will be assured by testing for aerobic and anaerobic bacteria, fungus and mycoplasma.

3) S+/L—assay must be negative.

4) Souther blot or PCR analysis will be run on the transduced tumor to assure that proviral sequences are present.

5) TNF protein assay to assure the production of TNF. Cells must be producing at least 100 pg TNF/$10^6$ cells/24 hours.

C. Injection of Tumor Cells.

Gene-modified tumor cells are harvested from the culture flasks by exposure to 0.25% versene (EDTA) for 10 minutes. The cells are washed three times by suspension in 50 mls normal saline and centrifugation. The final cell pellet will be suspended in normal saline and counted. $2\times10^8$ viable cells in 1 ml normal saline are injected subcutaneously just beneath the skin in the anterior mid thigh and the overlying skin marked with a tatoo dot. If $2\times10^8$ cells are not available, fewer may be given but not less than $2\times10^7$ cells will be injected. About 3 cm lateral or vertical to this injection the patient will receive two intradermal injections (separated by 1 cm) of $2\times10^7$ gene modified tumor cells in 0.1 ml normal saline and these sites also marked by a tatoo dot. These sites are monitored weekly by a physician. At three weeks the patient undergoes excisional biopsy of superficial inguinal lymph nodes (without formal dissection) in the area draining the inoculation site for growth of lymphocytes. If tumor grows at any of these sites they will be excised when they reach 1 to 2 cm for growth of TIL. If no tumor growth is evident that the sites of tumor injection will be excisionally biopsied at 8 weeks after injection of pathologic analysis.

D. Growth of Lymphocytes.

At least two days prior to surgery, peripheral blood lymphocytes are collected by leukapheresis for four hours, are processed, and then cultured as described in Example 4.

If, during the growth TIL, a patient's condition has deteriorated to an unacceptable level, or if the patient has developed significant cardiac, renal, pulmonary, or hematologic dysfunction, then the patient will not receive the infusion of TIL or of IL-2 as described hereinbelow.

When the total lymphocytes f r a patient are ready f r harvest, $5\times10^6$ cells are taken from cyt 1 gical examination. Cytospins are examined f r the presence f remaining tum r. At least 200 cells are studied and therapy proceeds only when no tumor cells are found. Other lymphocyte samples are taken f r characterization of cell surface markers and for assessment of cytotoxicity. (Berd, et al., Cancer Res., Vol. 46, pgs. 2572–2577 (1986)). Briefly, lymphocytes are stained with fluorescent-labeled antibodies (Leu2, Leu3, Lue4, Lye7, Lue11, Leu5, Leu9, LeuM3, HLADDR and Tac). Chromium release assays are performed with K562, Daudi autologous tumor, and allogeneic tumor targets.

To infuse the lymphocytes, they are thawed and grown for one to three additional weeks using the same procedures hereinabove described. For infusion TIL are reharvested. At the time of cell collection, one liter of saline for injection is pumped through the collection chamber and the centrifuge is stopped. Lymphocytes are resuspended in the collection bag, the centrifuge is started again, and another liter of saline is pumped through to wash fully the TIL's free of tissue culture medium components. The cells are then filtered through a platelet administration set into 600 ml transfer packs (Fenwal), and 50 ml of 25% albumin and 450,000 IU of IL-2 are added to the 200 to 300 ml volume of cells in saline. The TIL are infused over 30 to 60 minutes through a central venous catheter.

E. Administration of Interleukin-2.

The recombinant IL-2 used in this trial is provided by the Division of Cancer Treatment, National Cancer Institute (supplied by Cetus Corporation, Emeryville, Calif.) and will be administered exactly as specified in Rosenberg, et al., New Engl. J. Med., Vol. 323, pgs. 570–578 (1990). The IL-2 is provided as a lyophilized powder and will be reconstituted with 1.2 ml/vial. Each vial contains approximately 1.2 mg of IL-2 (specific activity $18\times10^6$IV/mg). Less than 0.04 ng of endotoxin are present per vial as measured by the limulus amebocyte assay. Each vial also contains 5% mannitol and approximately 130–230 μg of sodium dodecyl sulfate/mg of IL-2. Following reconstitution the IL-2 is diluted in 50 ml of normal saline containing 5% human serum albumin, and is infused intravenously at a dose of 720,000 IU/kg over a 15 minute period every 8 hr, beginning from two to 24 hr after the TIL infusion. IL-2 will be given for up to five consecutive days as tolerated. Under no circumstances is more than 15 doses of IL-2 be administered. Doses may be skipped depending on patient tolerance. Doses will be skipped if patients reach grade III or grade IV toxicity. If this toxicity is easily reversed by supportive measures then additional doses may be given.

Patients may receive concomitant medications to control side effects. For example, the patients may be given acetaminophen (650 mg every 4 hours), indomethacin (50–75 mg every 6 hours), and ranitidine (150 mg every 12 hours) throughout the course of the treatment. Patients may also receive intranveous meperidine (25–50 mg) to control chills if they occur. Hydroxyzine hydrochloride may be given (25 mg every 6 hours) to treat pruitia, if present.

EXAMPLE 7

In this example, the procedure of Example 6 were again followed, except that the vector employed to generate vector particles and retroviral vector supernatant, was the IL-2-NeoR vector. This vector was constructed from the vector LXSN (Miller, et al, 1989), and contains the Il-2 gene. Upon construction f the IL-2NeoR vector and the generation f vector particles and retroviral vector supernatants, that protocols for preparing gene-modified tumor cells and for treatment of patients with such cells, described in Example 6, were then followed.

Although the present invention has been described in particular with respect to genetically engineering primary human nucleated blood cells, and primary human tumor cells, it is to be understood that within the scope of the present invention, one may genetically engineer other human primary cells. Other primary human cells which may be genetically engineered in accordance with the present invention include, but are not limited to, endothelial cells, epithelial cells, keratinocytes, stem cells, hepatocytes, connective tissue cells, fibroblasts, mesenchymal cells, msothelial cells, and parenchymal cells.

While the invention has been described with respect to certain specific embodiment, it will be appreciated that many modifications and changes may be made by those skilled in the art without departing from the spirit of the invention. It is intended, therefore, by the appended claims to cover all such modification and changes as fall within the true spirit and scope of the invention.

What is claimed is:

[1. A process for providing a human with a therapeutic protein comprising:

introducing human cells int a human, said human cells having been treated in vitro to insert therein a DNA segment encoding a therapeutic protein said human cells expressing in vivo in said human a therapeutically effective amount of said therapeutic protein.]

[2. The process of claim 1 wherein said cells are blood cells.]

[3. The process of claim 1 wherein said cells are leukocytes.]

[4. The process of claim 1 wherein said cells are lymphocytes.]

[5. The process of claim 1 wherein said cells are T-lymphocytes.]

[6. The process of claim 1 wherein said cells are TIL cells.]

[7. The process of claim 1 wherein said cells are B-lymphocytes.]

[8. The process of any one of claims 1–7 wherein said DNA segment has been inserted into said cells in vitro by a viral vector.]

[9. The process of claim 8 wherein said viral vector is a retroviral vector.]

[10. The process of any one of claims 1–7 wherein the DNA segment encodes a cytokine.]

[11. The process of claim 10 wherein the cytokine is TNF.]

[12. The process of claim 10 wherein the cytokine is an interleukin.]

[13. The process of claim 10 wherein said DNA segment has been inserted into said cells in vitro by a viral vector.]

[14. The process f claim 13 wherein said viral vector is a retroviral vector.]

*15. A process for providing a human with a therapeutic protein comprising:*

*introducing autologous human cells into a human, said autologous human cells having been treated in vitro to insert therein a DNA segment encoding a therapeutic protein, said autologous human cells expressing in vivo in said human a therapeutically effective amount of said therapeutic protein, wherein said therapeutic protein is an interleukin, wherein the autologous human cells are T lymphocytes.*

*16. The process of claim 15, wherein said cells are tumor infiltrating lymphocytes (TIL).*

*17. The process of claim 15 or 16, wherein said DNA segment has been inserted into said cells in vitro by a viral vector.*

*18. The process of claim 17, wherein said viral vector is a retroviral vector.*

*19. The process of claim 15, wherein the interleukin is selected from the group consisting of IL-1, IL-2, IL-3, IL-4, IL-5, IL-6, IL-7, IL-8, IL-9, IL-10, IL-11, and IL-12.*

*20. The process of claim 19, wherein the interleukin is IL-2.*

* * * * *